United States Patent

Hill, Jr.

(10) Patent No.: US 8,134,127 B2
(45) Date of Patent: Mar. 13, 2012

(54) COMPACT HANDHELD NON-LASER DETECTOR FOR GREENHOUSE GASSES

(75) Inventor: Ralph Henry Hill, Jr., San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 0 days.

(21) Appl. No.: 13/194,492

(22) Filed: Jul. 29, 2011

(65) Prior Publication Data

US 2011/0278458 A1 Nov. 17, 2011

Related U.S. Application Data

(62) Division of application No. 12/381,768, filed on Mar. 16, 2009, now abandoned.

(51) Int. Cl.
 *G01J 5/02* (2006.01)
(52) U.S. Cl. ................................. 250/339.06
(58) Field of Classification Search .............. 250/339.06
 See application file for complete search history.

(56) References Cited

U.S. PATENT DOCUMENTS

| | | | |
|---|---|---|---|
| 3,585,436 A | 6/1971 | Beijer et al. | |
| 3,763,392 A | 10/1973 | Hollister | |
| 3,848,970 A | 11/1974 | Goodell | |
| 4,555,627 A | 11/1985 | McRae, Jr. | |
| 4,755,675 A | 7/1988 | Rosenfeld et al. | |
| 5,412,681 A | 5/1995 | Eisel et al. | |
| 5,523,569 A | 6/1996 | Hornfeld et al. | |
| 6,768,127 B1 | 7/2004 | Eggers et al. | |
| 2002/0071122 A1 | 6/2002 | Kulp et al. | |
| 2007/0018104 A1 | 1/2007 | Parvin et al. | |
| 2009/0127478 A1 | 5/2009 | Inoue et al. | |
| 2010/0230593 A1 | 9/2010 | Hill, Jr. | |
| 2010/0231722 A1 | 9/2010 | Hill, Jr. et al. | |

FOREIGN PATENT DOCUMENTS

WO   2007139022   12/2007

OTHER PUBLICATIONS

Nowak, et al, "The Temperature-Dependent Absorption Spectrum of the V3 Band of SF6 At 10-6 um+", J.Quant. Spectrosc. Radiat. Transfer. vol. 15, No. 10-E, pp. 945-961, Pergamon Press 1975. Printed in Great Britian.

"Spectral Remote Sensing and Detection"; home page; available at http://www.spectralcorp.com/index.html; retrieved Apr. 20, 2009.

"Spectral Remote Sensing and Detection"; EO/IR Products page; available at http://www.spectralcorp.com/html/eo_ir_products.html; retrieved Apr. 20, 2009.

(Continued)

*Primary Examiner* — David Porta
*Assistant Examiner* — Shun Lee
(74) *Attorney, Agent, or Firm* — Grossman, Tucker et al.

(57) ABSTRACT

Techniques are disclosed relating to gas leak detection. The techniques can be deployed, for example, in compact, handheld portable devices usable for detecting leaks in space-confined applications. The devices generally include a non-laser light source and thermal imaging camera that allow for detection of a target gas (or gasses) that absorbs at least some of the light source's wavelengths of operation. The light source can be implemented, for example, with an incoherent infrared (IR) light source, such as a resonance lamp configured with a gas cell containing a volume of a gas that, when excited by electric discharge, emits a wavelength that is absorbed by the target gas.

9 Claims, 5 Drawing Sheets

OTHER PUBLICATIONS

"Spectral Remote Sensing and Detection"; Gas Leak Detection page; available at http://www.spectralcorp.com/html/gas_leak_detection.html; retrieved Apr. 20, 2009.

"Spectral Remote Sensing and Detection"; BAGI Systems page; available at http://www.spectralcorp.com/html/bagi_systems.html; retrieved Apr. 20, 2009.

"Spectral Remote Sensing and Detection"; GasVue page; available at http://www.spectralcorp.com/html/_gasvue.html; retrieved Apr. 20, 2009.

"Spectral Remote Sensing and Detection"; GasVue II page; available at http://www.spectralcorp.com/html/_gasvue_ii.html; retrieved Apr. 20, 2009.

"Spectral Remote Sensing and Detection"; Laser Line-Scan Camera (LLC) page; available at http://www.spectralcorp.com/html/llc_systems.html; retrieved Apr. 20, 2009.

EIS, "Home, Welcome to Equipment Imaging and Solutions, Inc.," available at http://www.sf6detection.com/; retrieved on Nov. 19, 2008.

Access Laser Company, "Low Power CO2 Laser," available at http://www.accesslaserco.com/PDF/Spec%20Lasy3.pdf; retrieved on Nov. 19, 2008.

McRae, "Gas Value and the Magnesium Industry: Advanced SF6 Leak Detection," EPA Conference on SF6 and the Environment: Emission Reduction Strategies, San Diego, CA, Nov. 2-3, 2000; available at www.epa.gov/electricpower-sf6/documents/conf00_mcrae.pdf(Power Point Presentation).

Access Laser Company, "Products," available at http://www.accesslaserco.com/Products.htm; retrieved on Nov. 19, 2008.

"Absorption of Infrared Radiation," available at http://www.habmigern2003.info/future_trends/infrared_analyser/ndir/IR-Absorption-GB.html; retrieved, Dec. 15, 2008 (author unknown).

McRae, "GasVue and the Magnesium Industry: Advanced SF6 Leak Detection," available at www.epa.gov/electricpower-sf6/documents/conf00_mcrae_paper.pdf; retrieved on retrieved Nov. 18, 2009.

U.S. Non-Final Office Action issued Nov. 15, 2010 in U.S. Appl. No. 12/381,768 (pages).

U.S. Office Action issued Apr. 29, 2011 in related U.S. Appl. No. 12/381,768.

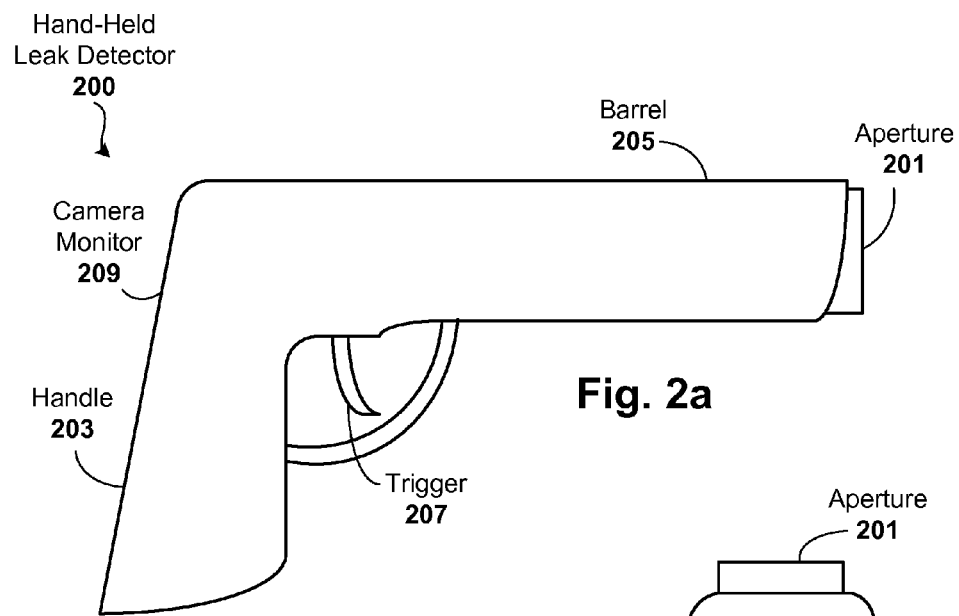
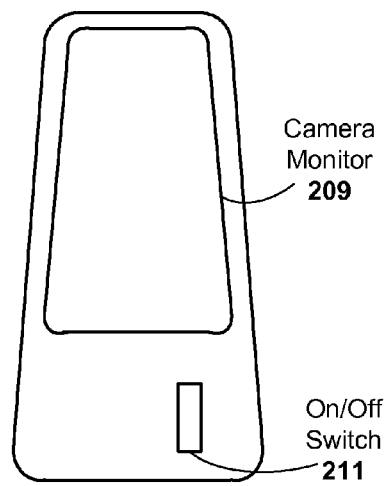
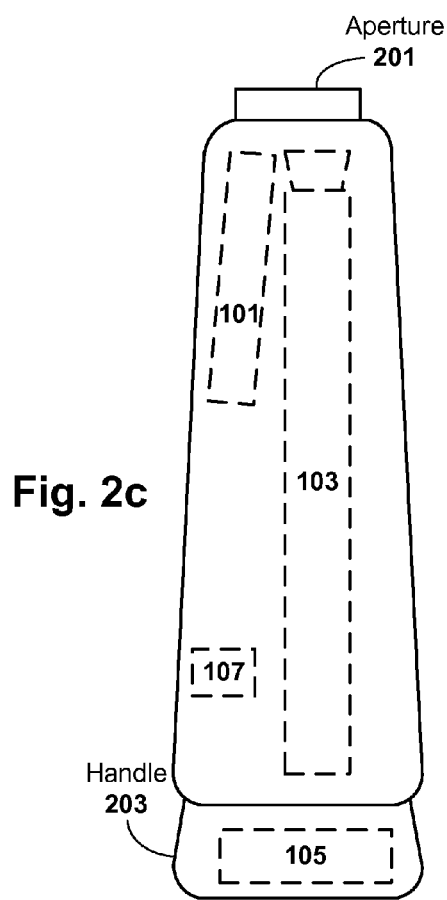

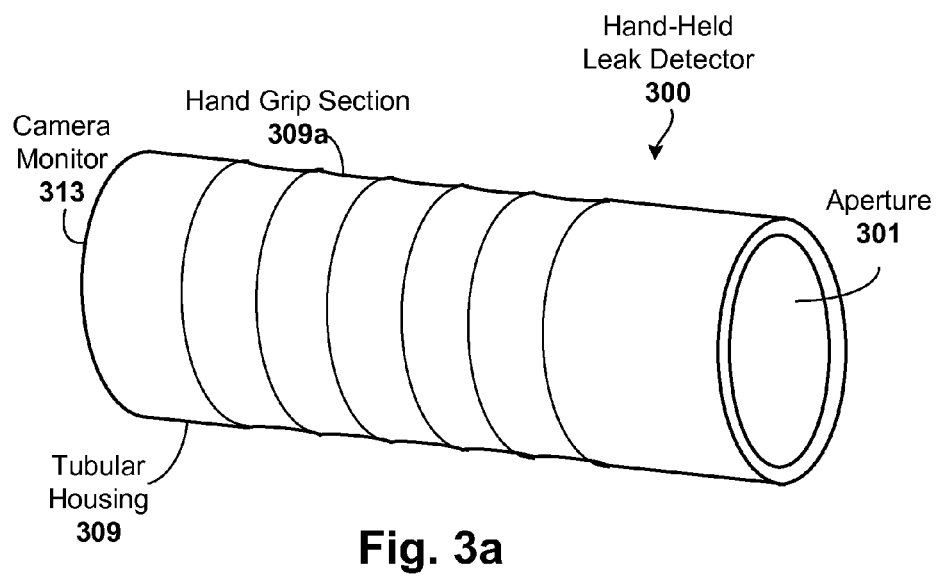
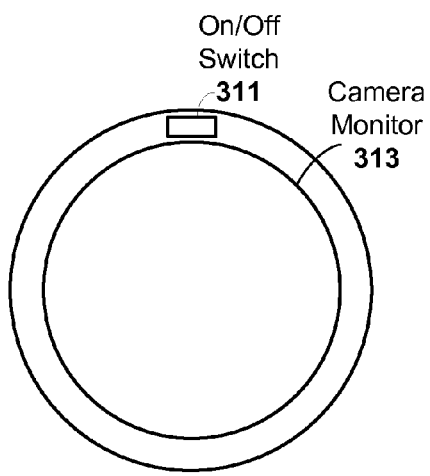
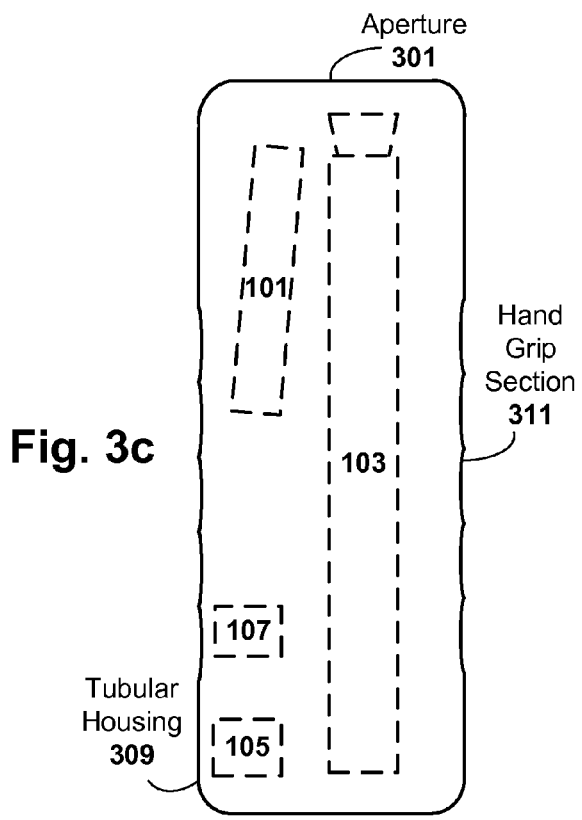

COMPACT HANDHELD NON-LASER DETECTOR FOR GREENHOUSE GASSES

RELATED APPLICATION

This application is a divisional of U.S. patent application Ser. No. 12/381,768, filed Mar. 16, 2009, and titled "Compact Handheld Non-Laser Detector for Greenhouse Gasses" which is herein incorporated by reference in its entirety.

STATEMENT OF GOVERNMENT INTEREST

The invention was made with United States Government support under contract DAAB07-03-D-B009 awarded by the U.S. Air Force, and the United States Government may have certain rights in this invention.

FIELD OF THE INVENTION

The invention relates to gas leak detection, and more particularly, to techniques that can be employed in compact, handheld devices for detecting leaks in relatively small spaces.

BACKGROUND OF THE INVENTION

There is presently a great need to locate leaks of so-called "greenhouse" gases such as sulfur hexafluoride ($SF_6$). As is generally known, higher concentrations of greenhouse gases in the atmosphere cause infrared (IR) radiation released from the earth to become trapped in the lower atmosphere. As a result of this trapped radiation, the lower atmosphere tends to warm, which in turn impacts the Earth's weather and climate. Other common greenhouse gasses generally caused by human activity include carbon dioxide ($CO_2$), methane ($CH_4$), chlorofluorocarbon (CFC), hydrofluorocarbon (HFC), and ozone ($O_3$).

In general, absorption techniques can be used to detect many such gases. However, there are a number of limitations associated with such conventional techniques. For instance, absorption techniques in the thermal IR range are not effective if the background temperature is similar to the temperature of the target gas to be detected, because there is almost no contrast between the background and the target gas. In addition, image contrast can be weak, caused by other factors, such as inhomogeneous illumination and weak absorption. Because of these problems, techniques to enhance the contrast have been proposed.

These conventional techniques generally increase the image contrast utilizing a laser illuminator. One such technique is provided in U.S. Pat. No. 4,555,627, titled "Backscatter Absorption Gas Imaging System," which describes absorption techniques to image hazardous gases. In particular, the disclosed technique uses a flying spot IR laser beam and video imaging system, and detects hazardous gases which are highly absorbed by the laser beam. Cameras based on similar techniques have been developed to detect $SF_6$ (e.g. GasVue and GasVue II camera product lines). However, these cameras are large and bulky (typically shoulder mounted units that are coupled to power and cooling units via heavy cabling), and therefore are application limited. For instance, such techniques cannot be implemented inside confined spaces or otherwise close quarters, such as within the fuselage of an airplane or other vehicle that may be equipped with gas-containing gear (e.g., radar equipment).

There is a need, therefore, for gas leak detection techniques that can be deployed, for example, in compact, handheld devices usable for detecting leaks in space-confined applications.

SUMMARY OF THE INVENTION

One embodiment of the present invention provides a gas leak imaging system. The system includes a non-laser incoherent light source for providing a light beam having at least one wavelength that is absorbable by a target gas, and a thermal imaging camera having a field of view and for imaging absorption of the at least one wavelength by the target gas. In general, the word "light" is used herein to include any output wavelength, such as infrared. The system is contained in a handheld housing (e.g., hand-gun or telescope shaped housing or other form factor suitable for handheld operations). The target gas can be, for example, sulfur hexafluoride ($SF_6$), or any other detectable gas using the techniques described herein. The camera can be, for example, a long-wave infrared camera. Other targets gasses and cameras will be apparent in light of this disclosure. In some cases, the light source may be further configured for expanding the light beam toward the field of view. In one specific case, the light source is a resonance lamp, including a cell that contains a volume of a gas (e.g., such as the target gas, or other gas or combination of gasses capable of emitting radiation that is in resonance with absorption lines of the target gas), an excitation coil wrapped with a number of turns around the cell, and an excitation source operatively coupled to the coil. In response to the excitation source energizing the coil, radiation is emitted from the cell that is in resonance with absorption lines of the target gas. In one specific such case, the resonance lamp is configured with a transmitting window for expanding the light beam toward the field of view, such that radiation emitted from the cell is transmitted by the transmitting window toward the field of view. The resonance lamp may further include a rear mirror for reflecting radiation within the cell toward the transmitting window. The transmitting window can be, for example, a germanium or zinc selenide diverging lens or flat window. In another such specific case, the volume of the target gas contained in the cell is the same as the target gas. The excitation source can be, for example, one of an RF oscillator or a pulse width modulation source or an RF waveguide excitation source. In another specific case, the non-laser incoherent light source is a modified laser. The laser can be modified, for instance, by replacing its output minor with a transmitting window for expanding the beam toward the field of view, and replacing its gaseous lasing medium with a gas capable of emitting radiation that is in resonance with absorption lines of the target gas. Thus, in one such example, the $CO_2$ of a $CO_2$ laser could be replaced by $SF_6$ or other suitable gas. Note that the replacement gas does not have to be the same as the target gas. Rather, the replacement gas can be any gas or combination of gasses which when excited emits a wavelength that is absorbed by the target gas.

Another embodiment of the present invention includes a gas leak imaging method. The method includes providing a light beam from a non-laser incoherent light source to a field of view, the light beam having at least one wavelength that is absorbable by a target gas. The method further includes expanding the light beam toward the field of view, and imaging absorption of the at least one wavelength by the target gas. The light source is contained in a handheld device (e.g., having a hand-gun or telescope shape, etc) that is capable of carrying out the method. In one such embodiment, the non-laser incoherent light source is a resonance lamp that includes a cell that contains a volume of a gas (e.g., target gas, or other gas or combination of gasses capable of emitting radiation that is in resonance with absorption lines of the target gas), an excitation coil wrapped with a number of turns around the cell, an excitation source operatively coupled to the coil, and a rear minor for reflecting radiation within the cell toward the transmitting window. In response to the excitation source energizing the coil, radiation is emitted from the cell that is in resonance with absorption lines of the target gas.

The features and advantages described herein are not all-inclusive and, in particular, many additional features and advantages will be apparent to one of ordinary skill in the art in view of the drawings, specification, and claims. Moreover, it should be noted that the language used in the specification has been principally selected for readability and instructional purposes, and not to limit the scope of the inventive subject matter.

BRIEF DESCRIPTION OF THE DRAWINGS

FIG. 2a is perspective view of a handheld gas leak detector, configured in accordance with another embodiment of the present invention.

FIG. 2b is end-view of the handheld gas leak detector shown in FIG. 2a.

FIG. 2c is top-view of the handheld gas leak detector shown in FIG. 2a, with internal components shown in dashed lines.

FIG. 3a is perspective view of a handheld gas leak detector, configured in accordance with another embodiment of the present invention.

FIG. 3b is end-view of the handheld gas leak detector shown in FIG. 3a.

FIG. 3c is top-view of the handheld gas leak detector shown in FIG. 3a, with internal components shown in dashed lines.

DETAILED DESCRIPTION OF THE INVENTION

Figure 1A:
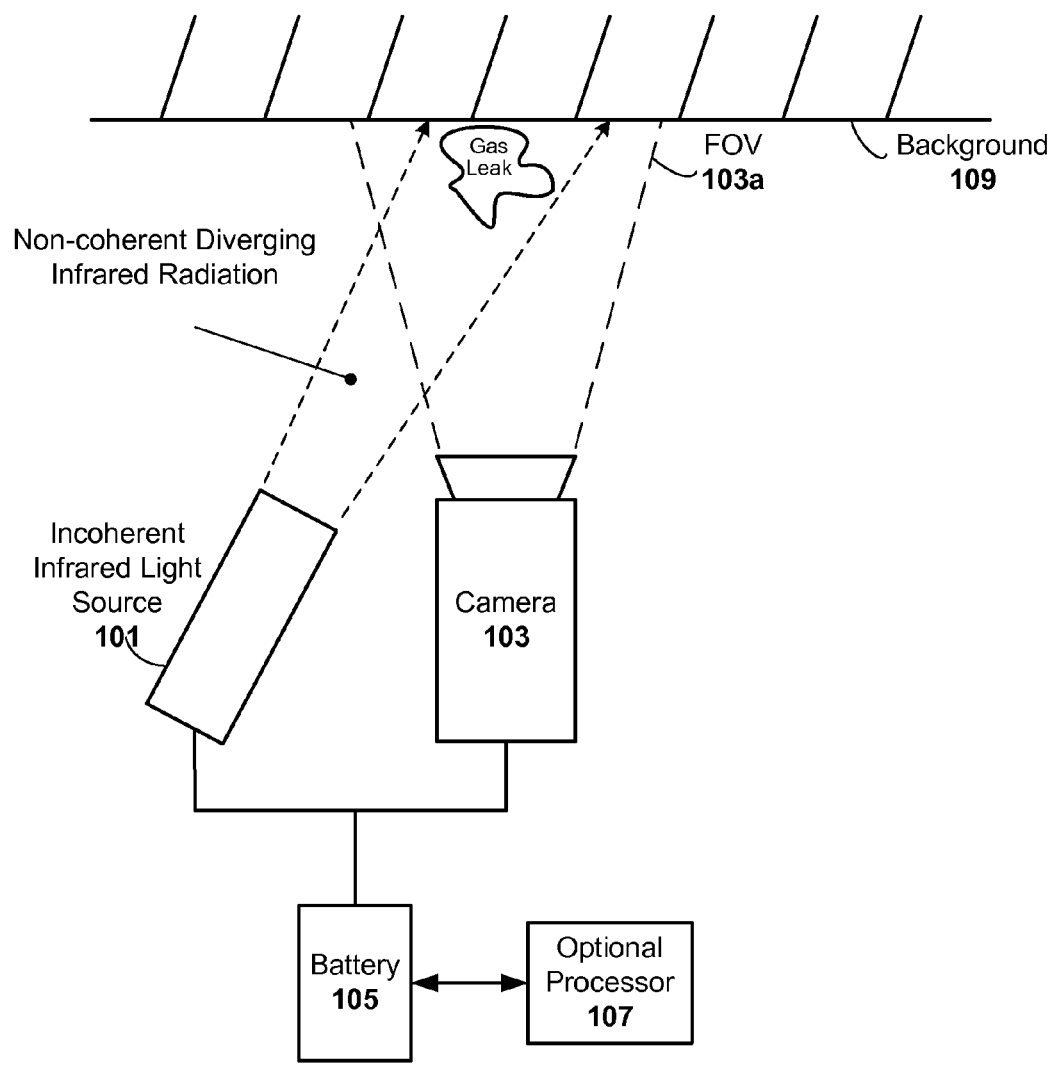
FIG. 1a is a laser-free gas leak detection system, configured in accordance with an embodiment of the present invention.

Techniques are disclosed relating to gas leak detection. The techniques can be deployed, for example, in compact, handheld portable devices usable for detecting leaks in space-confined applications. The devices generally include a non-laser light source and thermal imaging camera that allow for detection of gas that absorbs at least some of their wavelengths of operation. The light source can be implemented, for example, with an incoherent infrared (IR) light source, such as a resonance lamp configured with a gas cell containing a volume of the target gas. The techniques are suitable for use, for instance, in detecting gas leaks within the fuselage of an airplane or other vehicle that may be equipped with gas-containing gear (e.g., radar equipment), which may be leaking. Other such confined-space applications will be apparent in light of this disclosure.

General Overview

Imaging the infrared absorption of gasses such as $SF_6$ is generally known. However, as previously explained, such conventional detection techniques generally employ large units that are not suitable for space-confined applications. This longstanding design paradigm has generally not been challenged, as it is widely believed that gas leaks can be readily detected from a distance thereby allowing a nearby suitable and open space to be selected for the imaging and detection process to be carried out. Moreover, efforts to use smaller components (such as compact lasers) introduce a number of non-trivial problems.

For instance, conventional designs employ stabilized lasers which require cooling (e.g., water cooled lasers and air cooled lasers). Conventional cooling componentry tends to be bulky and heavy (e.g., cooling fans and/or water), and ultimately limits the form factor of the overall system to a relatively large size. An unstabilized (uncooled) laser will eliminate the need for such bulky/heavy cooling componentry associated with stabilized lasers, but is susceptible to wavelength hopping of the laser. In particular, an unstabilized laser may hop to a wavelength that is not absorbed by the target gas (e.g., $SF_6$, or other such greenhouse gas). The reason that the wavelengths hop around is because of thermal instabilities (given the lack of cooling). Another problem generally associated with using lasers in close quarters has to due with safety, and more specifically with the power density of the laser. For instance, there may be both a personnel hazard (e.g., eye safety) as well as a fire hazard.

Thus, and in accordance with one example embodiment of the present invention, a gas leak imaging system is provided that employs a relatively small non-laser light source that is not susceptible to wavelength hopping and/or safety issues that might be associated with high power density laser light. The non-laser light source can be implemented, for example, with a resonance lamp or other suitable incoherent infrared (IR) light source. A transmitting window or lens can be provided on the output of the light source to expand the beam toward the field of view, and a thermal camera can be used to image the IR absorption of the target gas or gasses. The system is compact and can be implemented in a handheld unit (e.g., having a form factor similar to that of a hand-gun or telescope) that can be brought into small spaces and aimed at target areas to carryout inspection and leak detection. In some such embodiments, the light source can be implemented within the infrared camera. In a more general sense, the functional components making up the system can be integrated into a compact housing suitable for handheld applications or otherwise in close quarters.

By using an incoherent infrared light source to in place of laser light, the potential problems associated with lasers are avoided. Note that laser safety issues may not actually be serious issues (depending on laser power density, wavelength of operation, safety precautions taken, etc); however, there may be a perception of safety issues that are generally associated with laser light that is difficult to overcome, thereby impeding widespread usage of laser-based techniques. Therefore, embodiments of the present invention employ a non-laser IR light source capable of being used to image infrared-absorbing leaks.

System Architecture

FIG. 1a is a laser-free gas leak detection system, configured in accordance with an embodiment of the present invention.

As can be seen, the system includes a thermal imaging camera 103 having a field of view (FOV) 103a, and an incoherent IR light source 101. The system also includes a battery 105, which is connected to any components requiring power (e.g., camera 103, light source 101, and processor 107). Battery 105 may also be operatively coupled to processor 107 for control purposes (e.g., power management scheme that is executed by processor 107).

In operation, the gas leak imaging system can be used to detect gas leaks by directing a diverging beam of incoherent IR light from light source 101 toward the FOV 103a of camera 103 and toward the background area 109 (which can be any area place leaks of the target gas might be). The IR light beam can be expanded by diverging optics included in the source 101. When the light beam is projected into the FOV 103a, the infrared absorption of the leaking gas is imaged by the infrared camera 103 (e.g., FIG. 4). The light source 101 can be, for example, a resonance lamp configured with a gas cell containing a volume of the target gas to be detected that can be excited using an electric discharge external to the cell containing the gas. The camera 103 can be, for example, a longwave infrared camera, thereby allowing the system to image the infrared absorption of a target gas absorbable within that range. In one such specific embodiment, the light source 101 is implemented with a resonance lamp configured with a gas cell containing a few Torr of $SF_6$, and the longwave IR camera 103 is implemented with a FLIR GasFindIR-LW, FLIR model 65HS (from FLIR Systems, Inc), or a Fluke model Ti55 (from Fluke Corporation). The light source 101 may include optics configured for the wavelength range of interest (e.g., 10.5 and 10.7 microns), and in one example case includes transmitting window in the form of a zinc selenide (ZnSe) diverging lens or flat window. Thus, the system can be implemented with a small non-laser IR light source and an IR camera. Other such suitable compact incoherent IR light sources and thermal imaging cameras can be used as well, depending on factors such as target gas to be detected. The battery 105 can be implemented with conventional technology (e.g., rechargeable NiMH or Li-ion batteries), and is capable of providing sufficient power to the system. In some embodiments, battery 105 may be distributed, wherein individual components making up the system each have their own battery. Conventional power conditioning techniques may also be employed, if so desired (e.g., regulation, filtering, etc). An AC adapter may also be provided for charging the battery 105 (or batteries). Numerous suitable variations and alternative power schemes can be used here.

Thus, a compact portable gas leak imaging system is provided. Any number of gas leaks can be detected depending on the system configuration. In one specific example embodiment, $SF_6$ leaks can be detected on the order of 1 sccm (standard cubic centimeter per minute) or less using a resonance lamp having a $SF_6$ gas cell and a zinc selenide transmitting window (for light source 101), and a FLIR model 65 HS longwave infrared camera (for camera 103). The entire system weighs about 10 lbs or less and can be easily handheld. Example form factors for the housing containing the system include a hand-gun or telescope shaped housing, although any number of suitable form factors can be used. Thus, handheld as used herein means that the system (or device, apparatus, etc) is small and light enough to be operated while an appropriate user holds it in one or both hands. An appropriate user may be, for instance, a man or woman capable of holding about 10 lbs in one or both hands (e.g., while arms are extended in front of the user or while the user's elbows are supported on a table or other suitable surface). Note that the system may optionally include, for example, a lanyard (cord worn around the neck and operatively coupled to the system) so that the system can hang from the lanyard during periods of non-use, and even while being used or otherwise manipulated by the user's hand or hands. A small tripod may also be used to support such a compact system, if so desired. The system can be operated, for example, to view targets in close proximity (e.g., less than a meter away), although viewing target areas at greater distances away (e.g., three meters or more) is possible as well using the appropriate optics, if needed and as will be apparent in light of this disclosure. In one specific such embodiment, the target wavelength operation is near 10.551 microns.

The system shown in FIG. 1a also includes an optional processor 107, which can be used to enable or otherwise select certain modes of operation (e.g., by enabling light source 101 and/or camera 103), and/or implement other functionality such as power conservation schemes for conserving power and report generation. The processor 107 may be implemented, for example, with a conventional processing environment such as a programmable gate array (e.g., ASIC or FPGA) or a microcontroller having a number of input/output ports and executable routines for carrying out desired functionality. The processor 107 may operate in conjunction with a user interface that allows the user to configure a desired mode of operation. This interface can be, for example, hardware-based (e.g., toggle switches that can be set to enable/disable modes of operation) or software-based (e.g., graphical user interface that can be manipulated to enable/disable modes of operation). In one particular embodiment, the processor 107 responds to user input to activate the detection system (e.g., by enabling the light source 101 and/or camera 103). In addition, should the detection system remain dormant (unused) for a period of time, the processor 107 may be configured to implement a power conservation scheme, where light source 101 and camera 103 are disabled to a low-power (or no-power) consumption mode. Such conservation schemes will help preserve the life of battery 105. Numerous other such configurations and functions for processor 107 will be apparent in light of this disclosure.

Incoherent IR Light Source

Figure 1B:
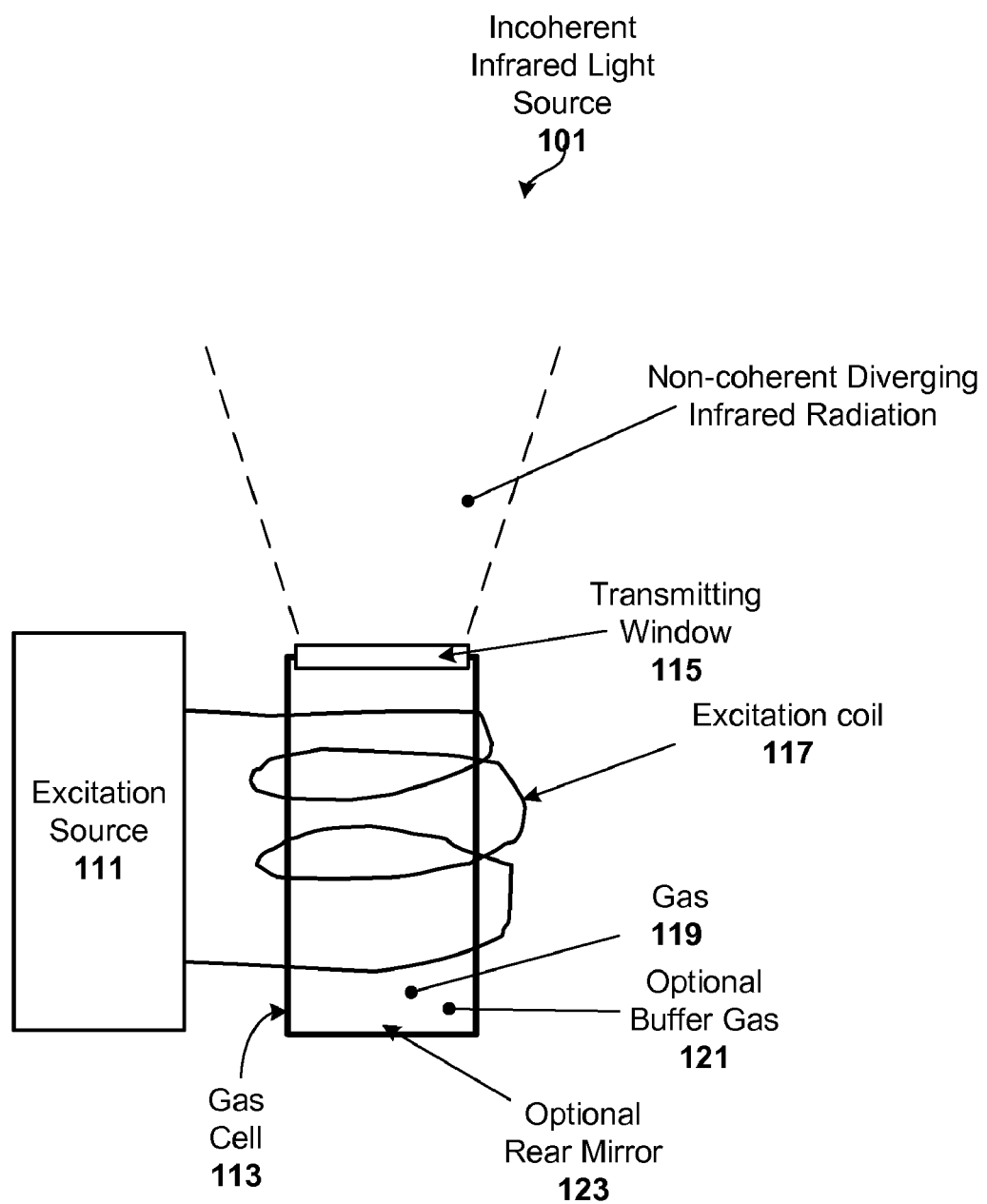
FIG. 1b is an example incoherent infrared light source of the system shown in FIG. 1a, configured in accordance with an embodiment of the present invention.

The general concept of resonance lamps has been known for a long time. However, such lamps have not been used in the context of gas leak detection. FIG. 1b is an example incoherent infrared light source 101 of the system shown in FIG. 1a, configured as a resonance lamp in accordance with an embodiment of the present invention. As can be seen, the light source 101 includes a glass vacuum cell 113 that contains a gas 119, and optionally contains a buffer gas 121. The cell 113 is wrapped with a number of turns (e.g., 2 to 6 turns) of an excitation coil 117 (e.g., heavy wire), which is driven by an excitation source 111.

In operation, the gas 119 within cell 113 is heated by energizing the excitation coil 117 (with source 111) so that enough of the gas 119 (typically millitorr) is vaporized in the glass cell 113 (or is already a vapor, as is the case with $SF_6$ at room temperature). Gas 119 can be, for example, the same as the target gas. One advantage of such an arrangement is that the radiation emitted from the excited gas 119 is in resonance with absorption lines of the target gas. In other embodiments, gas 119 is not the target gas, but is any other gas or combination of gasses that, when excited by electric discharge, emits a wavelength that is absorbed by the target gas. In any such cases, the emitted radiation can be used to effectively illuminate a gas leak that includes the target gas, by way of imaging the absorption of emitted radiation by the gas leak. In addition, note that no tuning is needed, since many of the emission lines are in resonance with the absorption lines (assuming most of the gas is in the ground state). In some cases, further note that the temperature of the gas may slightly influence absorption. Conventional temperature control and management techniques can be used, if so desired. In any case, the radiation emitted from the cell 113 is transmitted by transmitting window 115 toward the FOV 103a. The optional rear minor 123 can be used to reflect radiation within the cell 113 toward the transmitting window 115, so as to further optimize emission from the cell 113.

In one specific embodiment, the cell 113 contains $SF_6$ (e.g., a few Torr). An optional inert buffer gas 121 may also be used (e.g., at a few Torr pressure), to help maintain a stable discharge. Neon or argon are examples of buffer gas 121. The excitation source 111 can be implemented, for example, with a 27-MHz RF oscillator, a 15-KHz pulse width modulation source, a Tesla coil excitation scheme, or other such suitable means for providing an electric discharge external to the cell 113 containing the gas 119 (and possibly gas 121). Since the emission lines of interest in this example embodiment are in the infrared region, an infrared transmitting window 115 is provided. This transmitting window 115 can be implemented, for instance, as a diverging lens or flat window made of germanium (Ge) or zinc selenide (ZnSe) or other optically suitable materials.

In one such example embodiment, the light source 101 is implemented by modifying a small $CO_2$ laser (e.g., an unstabilized RF excited nominal 10.6-micron $CO_2$ laser, such as the Lasy-3 laser from Access Laser Company). In particular, the laser can be modified by replacing the $CO_2$ with $SF_6$, and replacing the output mirror with a Ge or ZnSe transmitting window 115. Note that this modified version would no longer be a laser, but would now be an incoherent IR source. An advantage would be that most all of the emission lines of the light source 101 would be absorbed by the leaking $SF_6$ gas (within the FOV 103a), and thus readily visible with the longwave thermal camera 103. This resonant lamp would be small and lightweight, estimated to be less than 4 lbs. As will be appreciated in light of this disclosure, the techniques described herein can be used with other gasses as well. Other such modification schemes will be apparent in light of this disclosure, wherein a laser source is modified by replacing its output mirror with a transmitting window for expanding the beam toward the FOV 103a, and by replacing its gaseous lasing medium with the target gas (or some other appropriate gas or combination of gasses that, when excited by electric discharge, emits a wavelength that is absorbed by the target gas).

Other combinations of gases and excitation sources are possible, as will be apparent in light of this disclosure. For example, a metal gas container may be used with a RF waveguide excitation source. Any gas or combination of gases can be used in the container, so long as the excited gas in the container (whether the container is glass, metal, or other suitable material) emits radiation that is absorbed by the target gas. In some cases, note that the contained gas of the non-laser incoherent source may be different from the target gas. For instance, there may be cases where using the target gas in the cell is not the best choice, because of the various wavelengths that get excited by the various kinds of discharge (e.g., accidental resonances).

Handheld System

FIGS. 2a, 2b, and 2c demonstrate a handheld gas leak detector 200 that includes the detection system shown in FIG. 1a, configured in accordance with an embodiment of the present invention. As can be seen, the detector 200 is shaped like a gun having a handle 203 and barrel 205, so as to allow a user to point the aperture 201 at a target area to search for leaks. The detector 200 can be powered on and off by switch 211, which effectively can be used to mechanically switch the battery 105 in and out of circuit, such that when switch 211 is on, detector 200 can be trigger operated, and when switch 211 is off, detector 200 can be stored or otherwise dormant. A number of operational schemes can be used here.

For instance, in one such example embodiment, when trigger 207 is pressed, an enable signal is provided directly to the light source 101 and camera 103 (and to any other supporting circuitry that needs to be enabled), so that leaks can be detected as described herein. In other cases, depressing the trigger 207 can be used to activate the optional processor 107, which then in turn enables the various components of the detection system to operate for leak detection purposes.

In any such cases, when the trigger 207 is pressed, a diverging beam of incoherent IR radiation from light source 101 passes through the aperture 201 to the target area within the FOV 103a of camera 103. Should the target gas be present, that gas will absorb radiation of the non-coherent diverging IR beam, thereby allowing the thermal camera 103 to image the gas leak. The gas leak will then appear on the camera monitor 209 (which may be internal or external to camera 103). As can be seen in FIG. 2c, the various components of the detection system can be integrated into the handheld gun-like housing. Any number of suitable component layouts can be used, depending on factors such as included functionality and number of options employed as well as the housing form factor and amount of available space therein.

FIGS. 3a, 3b, and 3c demonstrate a handheld gas leak detector 300 that includes the detection system shown in FIG. 1a, configured in accordance with another embodiment of the present invention. As can be seen, the detector 300 includes tubular housing 309 having a hand grip section 309a, and is configured to allow a user to point the aperture 301 at a target area to search for leaks. In alternative embodiments, housing 309 could be more square or rectangular in nature (as opposed to tubular). Other housing shapes amenable to handheld operation will be apparent in light of this disclosure. The detector 300 can be powered on and off by switch 311, which effectively can be used to mechanically switch the battery 105 in and out of circuit, such that when switch 311 is on, detector 300 is operational, and when switch 311 is off, detector 300 can be stored or otherwise dormant. A number of operational schemes can be used here.

For instance, in one such example embodiment, when switch 311 is pressed or otherwise turned on, an enable signal is provided directly to the light source 101 and camera 103 (and to any other supporting circuitry that needs to be enabled), so that leaks can be detected as described herein. In other cases, depressing the switch 311 can be used to activate the optional processor 107, which then in turn enables the various components of the detection system to operate for leak detection purposes. Note that the position of switch 311 can be moved to the side of the tube 309 (e.g., within the grip section 311) for convenient access by user.

In any such cases, when the switch 311 is activated, a diverging beam of incoherent IR radiation from light source 101 passes through the aperture 301 to the target area within the FOV 103a of camera 103. Should the target gas be present, that gas will absorb radiation of the non-coherent diverging IR beam, thereby allowing the thermal camera 103 to image the gas leak. The gas leak will then appear on the camera monitor 313 (which may be internal or external to camera 103). As can be seen in FIG. 3c, the various components of the detection system can be integrated into the handheld tubular housing 309. Any number of suitable component layouts can be used, depending on factors such as included functionality and number of options employed as well as the housing form factor and amount of available space therein.

Figure 4:
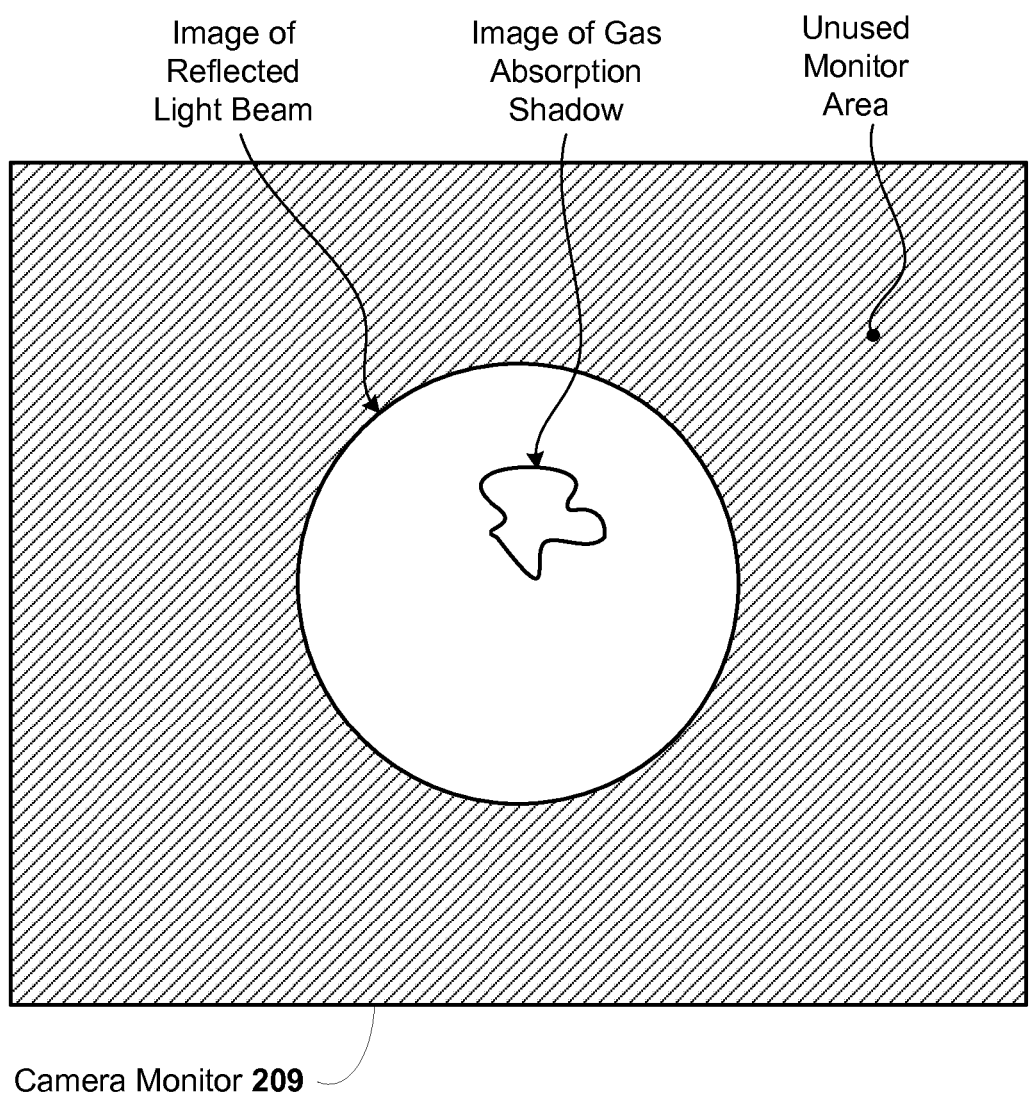
FIG. 4 illustrates an image of the infrared absorption of a gas detected by the system shown in FIG. 1a, in accordance with an embodiment of the present invention.

FIG. 4 illustrates an image of the infrared absorption of a gas detected by the system shown in FIG. 1a, in accordance with an example embodiment of the present invention. As can be seen, monitor 209 is square in this example embodiment, but other embodiments may have different shaped monitors. As can further be seen, the beam from light source 101 is round, such that the image of the reflected light beam shown on the monitor 209 is round also. Other embodiments may have different shaped light beams (square, etc) and/or monitors (such as the round monitor 313). The image of the gas absorption shadow can also be seen, thereby allowing a user to visually detect gas leaks. There may also be a portion of unused monitor area, as further shown.

The foregoing description of the embodiments of the invention has been presented for the purposes of illustration and description. It is not intended to be exhaustive or to limit the invention to the precise form disclosed. Many modifications and variations are possible in light of this disclosure. It is intended that the scope of the invention be limited not by this detailed description, but rather by the claims appended hereto.

What is claimed is:

1. A gas leak imaging method, comprising:
   supplying a laser;
   modifying said laser to produce a non-laser incoherent light source, wherein said modifying comprises:
     replacing an output mirror of said laser with a transmitting window; and
     replacing a gaseous lasing medium of said laser with a resonance gas capable of emitting radiation that is in resonance with absorption lines of a target gas and wherein at least one wavelength is in the range of 10.5 to 10.7 microns;
   providing a light beam from said non-laser incoherent light source, said light beam having said at least one wavelength that is absorbable by said target gas;
   providing a thermal imaging camera having a field of view and for imaging absorption of said at least one wavelength by said target gas; and
   containing said non-laser incoherent light source and said thermal imaging camera in a handheld housing.

2. The method of claim 1 wherein said target gas is sulfur hexafluoride ($SF_6$).

3. The method of claim 1 wherein said non-laser incoherent light source is configured for expanding said light beam toward said field of view.

4. The method of claim 1 wherein said camera is a long-wave infrared camera.

5. The method of claim 1 wherein said non-laser incoherent light source is $CO_2$ laser wherein the $CO_2$ is replaced with $SF_6$.

6. The method of claim 1 wherein said transmitting window is configured for expanding said light beam toward said field of view.

7. The method of claim 6 wherein said transmitting window is a germanium or zinc selenide diverging lens.

8. The method of claim 1 wherein said non-laser incoherent light source is less than 4 lbs.

9. The method of claim 1 wherein said resonance gas comprises a combination of gases.

* * * * *